(12) United States Patent
Gao

(10) Patent No.: US 8,371,849 B2
(45) Date of Patent: Feb. 12, 2013

(54) METHOD AND SYSTEM OF ANATOMY MODELING FOR DENTAL IMPLANT TREATMENT PLANNING

(76) Inventor: Fei Gao, Cypress, CA (US)

( * ) Notice: Subject to any disclaimer, the term of this patent is extended or adjusted under 35 U.S.C. 154(b) by 315 days.

(21) Appl. No.: 12/911,895

(22) Filed: Oct. 26, 2010

(65) Prior Publication Data

US 2012/0100500 A1  Apr. 26, 2012

(51) Int. Cl.
*G06G 7/60* (2006.01)
(52) U.S. Cl. .............................. 433/72; 433/213; 703/11
(58) Field of Classification Search .................. None
See application file for complete search history.

(56) References Cited

U.S. PATENT DOCUMENTS

2010/0105011 A1* 4/2010 Karkar et al. ................. 433/215

* cited by examiner

*Primary Examiner* — Stephen R Koziol
*Assistant Examiner* — Amandeep Saini
(74) *Attorney, Agent, or Firm* — GuideMia Technologies, LLC

(57) ABSTRACT

A method and a dental implant treatment planning and surgical guide design system based on a full anatomy model (FAM). A FAM consists of models for bones, teeth, and nerves, and a virtual stone model. A virtual stone model is not only a surface model of the soft tissue and tooth surfaces of a patient, but also a color map of tissue thickness data. It also contains the insert direction of a surgical guide. The treatment planning and surgical guide system uses the full anatomy model as a unique reference throughout the workflow. Its implant placement, restoration preview and surgical guide design are all based on the anatomy model.

9 Claims, 14 Drawing Sheets

Full Anatomy Model Components

|  | Fully Edentulous Lower Jaw | Fully Edentulous Upper Jaw | Partially Edentulous Lower Jaw | Partially Edentulous Upper Jaw |
|---|---|---|---|---|
| Soft Tissues | ✓ | ✓ | ✓ | ✓ |
| Bones | ✓ | ✓ | ✓ | ✓ |
| Teeth |  |  | ✓ | ✓ |
| Nerves | ✓ |  | ✓ |  |

FIG. 1

Embodiments of FAM

|  | Tissue | Bone | Tooth | Nerve | Tissue-Tooth | Bone-Tooth |
|---|---|---|---|---|---|---|
| Fully Edentulous Lower Jaw | ✓ | ✓ |  | ✓ |  |  |
| Fully Edentulous Upper Jaw | ✓ | ✓ |  |  |  |  |
| Partially Edentulous Lower Jaw | ✓ | ✓ | ✓ | ✓ |  |  |
|  |  |  |  | ✓ | ✓ | ✓ |
| Partially Edentulous Upper Jaw | ✓ | ✓ | ✓ |  |  |  |
|  |  |  |  |  | ✓ | ✓ |

FIG. 2

Data Source and Modeling Techniques of a FAM

| | Bone | Tooth | Bone-Tooth | Soft Tissue | Tissue-Tooth | Nerve |
|---|---|---|---|---|---|---|
| Patient CT Scan | Thresholding, removing scatter and contouring | Thresholding, removing scatter and contouring | Thresholding, removing scatter and contouring | | | Thresholding and Contouring, Manual drawing or path tracking |
| Radiographic Guide CT scan | | Thresholding, Contouring, Selection and Trimming, Marker-based registration | | Virtual Stone Model, Marker-based registration | | |
| Radiographic Guide optical scan | | Face selection and trimming, surface registration | | Virtual Stone Model, Surface registration | | |
| Plaster Model or Impression optical scan | | | | Face selection and trimming, Surface registration | | |
| Patient Intra-oral scan | | | | | | |

FIG. 9

METHOD AND SYSTEM OF ANATOMY MODELING FOR DENTAL IMPLANT TREATMENT PLANNING

CROSS-REFERENCE TO RELATED APPLICATIONS

| U.S. patent application Ser. No. 12,860,019 | Aug. 20, 2010 | Gao |
| U.S. patent application Ser. No. 12,795,045 | Jun. 7, 2010 | Gao |
| U.S. patent application Ser. No. 12,776,544 | May 10, 2010 | Gao |

REFERENCE CITED

US Patent Documents

| US 2007/0059665 A1 | Mar. 15, 2007 | Orentlicher et al. |
| US 2008/0193896 A1 | Aug. 14, 2008 | Yang et al. |
| U.S. Pat. No. 7,758,345B1 | Jul. 20, 2010 | Christensen |

OTHER PUBLICATIONS

Materialise, Dual scan protocol—Cone Beam CT, 2010

Philippe B. Tardieu, DDS, Alan L. Rosenfeld, DDS, The Art of Computer-guided implantology. Quintessence Publishing Co, Inc, 2009

Zhengyou Zhang, Iterative point matching for registration of free-form curves and surfaces Source. International Journal of Computer Vision, Volume 13, Issue 2 (October 1994)

Luis Ibanez, Will Schroeder, et al. ITK software guide, Second Edition, the Insight Software Consortium, 2005

FIELD OF THE INVENTION

This invention concerns the methodology of computerized image-guided dental implant treatment planning. It discloses a method to create geometric models of oral-dental anatomy structures, and to simulate the implant placement, restoration preview, and surgical guide CAD/CAM with anatomy models. This invention is to address the issue that those three major tasks in treatment planning systems are not based on same unique geometric models. The center of the solution is comprehensive oral-dental anatomy modeling and its results—full anatomy models (FAM). With FAM, the treatment planning system will seamlessly integrate implant placement with restoration preview and surgical guide design.

BACKGROUND OF THE INVENTION

Dental implant treatment planning software systems normally work in two modes, single scan or dual scan. With single scan protocol, a patient is CT-scanned, the DICOM files are loaded into a software system, the jaw bone structure and remaining teeth are segmented and modeled in 3D space, and implant placements are simulated with the 3D bone/tooth model and the DICOM slices. In the dual scan mode, a so-called radiographic guide is made with radio-opaque markers. The patient is scanned wearing the radiographic guide, and the guide is then scanned separately. When the DICOM files are loaded into the system, the 3D bone/tooth model is created, the radiographic guide model is generated, and implants are placed with references to the 2D slices and the 3D model. More details of these workflows can be found in publications (Materialise, Philippe B Tardieu, etc.) and software documents of SimPlant, NobelGuide and EasyGuide, etc., which are the state-of-the-art of such workflows. All of the systems would place implants with 2D slices. SimPlant introduced 3D implant placement recently.

Very few publications are relevant to the topic that how implants are placed with references to CT scans data. Orentlicher (US 2007/0059665 A1) described a workflow in which CT scans are converted into files of some format, and doctors/technicians can download the converted files to place implants. Technically, this is same as what SimPlant has implemented. The converted files are the bone/tooth model and 2D slices, so the implant placement is based on the 2D slices and 3D bone/tooth model. Yang (US 2008/0193896) disclosed an approach trying to combine the CT scan data with physical cast models, which is related to the idea that implants need to be placed with references to the actual geometry of the patient's anatomy including soft tissues.

Another area of treatment planning system is the restoration preview. The idea is to put together a patient's anatomy structure, implants, abutments, and crowns to preview and evaluate the aesthetics of a treatment plan. The software function to add virtual teeth to the 3D graphics views can be found in commercial systems (www.materialise.com.Dental, SimPlant from Materialise). Unfortunately, the virtual teeth are added to a model with only jaw bones and teeth, other than a model that also includes soft tissues. This makes the virtual tooth functionality inconsistent with the actual needs of aesthetics evaluation.

As far as the soft tissue model is concerned, Christensen (U.S. Pat. No. 7,758,345B1) disclosed an approach to create a physical model with both bone and soft tissues from imaging data. A hard tissue model is created from scan data. So is a scan prosthesis (or radiographic guide in this disclosure) model. The hard tissue model is modified with some supporting structures, then the model of the scan prosthesis is attached to it, and finally "moldable" material is used to mold a model of the patient's soft tissue between the three-dimensional model of the scan prosthesis and the modified hard tissue model by pressing the three-dimensional model of the scan prosthesis against the one or more support structures.

From the implant placement to the restoration preview, surgical guide CAD/CAM, and implant surgery, there are three references involved. First is the implant placement reference. If the implants are placed with 2D DICOM slices, the slice data is the placement reference. If the 3D model combining jaw bones and teeth is used, in other words implants are placed in a 3D graphics view of the 3D model, this model would be the placement reference. The second reference is called "aesthetics reference" in the remainder of this document, which is basically a duplicate of the patients' anatomy including soft tissues. When the aesthetics of an implant case is assessed, one would like to see how the implants and restorations go along with the soft tissues. Using combinations of bone and teeth as aesthetics references is not a good practice, but has been the reality in prior art since the tissue models were not available. The third reference is the base model that is used to create a surgical guide. For a single scan case, the bone/tooth model will be trimmed and offset and drilled to create a surgical guide, so the surgical guide reference is the bone/tooth model. For dual scan cases, the model of the radiographic guide is registered with the bone structure, and then used as the base for the surgical guide.

With the state-of-art treatment planning, the placement reference may not be the surgical guide reference, and the aesthetics reference does not actually exist in treatment planning systems, which makes it impossible to preview restorations with the actual patient anatomy. The digital modeling of soft tissues, as well as its usage in planning stage, is missing in the implant planning systems and techniques.

BRIEF SUMMARY OF THE INVENTION

The objective of this invention is to develop a methodology and the enabling algorithms to place implants, preview restorations and design surgical guides with the same reference model throughout the treatment planning workflow, regardless the underlying implant case is fully or partially edentulous, regardless whether a tissue-borne or bone-borne surgical guide is needed. This model will need to contain all oral-dental anatomy components of a patient, which are necessary for the treatment planning. The software system implementing this methodology is another part of this invention, which enables more efficient implant placements, better case assessments, and a consistent surgical guide modeling that works for all kinds of cases.

The center of this methodology is the comprehensive oral-dental anatomy modeling that creates a geometric model consisting of a patient's bone structure, nerve channels, soft tissues and remaining teeth. This model serves as the reference for implant placement, restoration preview and the CAD/CAM of surgical guides. In the remainder of this disclosure, this model is referred as Full Anatomy Model, or FAM. The essential difference between FAM and the geometric models in published systems is the soft tissue model.

In one embodiment, the soft tissue component of a FAM is extracted from the scan of a radiographic guide (scan prosthesis, provisional denture, etc). Either a CT scan or an optical scan can be used. Alternatively, the soft tissue model is obtained by the optical scan of a plaster model or an impression. The soft tissue model and bone model are assembled into one virtual stone model. Nerve models can then further be added to this assembly. Another embodiment is to use the patient's intra-oral scan, which seems more promising in terms of accuracy and efficiency. The intra-oral scan, impression scan and plaster model scan are all referred as optical scan in the remainder of this document.

The components of a FAM need to be aligned with the patient CT scan in a single coordinate system. This is an important aspect of anatomy modeling. The data sources—patient scan, radiographic scan or optical scans—are all different, so are the FAM components. Registration tools are used to align them. For example, with dual scan protocols, the markers of the radiographic guide will show up in the patient scan and the guide scan. A landmark based registration tool will identify markers, match them and align the patient data and the guide data.

The software system to create a FAM has modules corresponding to all the anatomy components. In order to define a case, the software has components to load patient CT scan, radiographic guide CT scan, or additional optical scans. There is at least one tool to generate the soft tissue model from radiographic guide CT scan, or any optical scan. Alternatively an optical scan can be directly used as the tissue model. A registration module will register the tissue model with the patient CT scan so that the components of a FAM can be assembled together. A surgical guide CAD component will generate a surgical guide model from the FAM. What differentiates the software is that this unique FAM is used as the references for implant placements, assessment and surgical guide CAD/CAM.

DESCRIPTION OF THE DRAWINGS

FIG. 1 lists the components of a FAM (Full Anatomy Model). It has all the anatomy structures that are necessary for treatment planning: jaw bones, teeth, soft tissues, and nerves if applicable.

FIG. 2 lists the embodiments of FAM. For example, a "Partially Edentulous Lower Jaw" case can be represented as a nerve model, a tissue-tooth model and a bone-tooth model.

FIG. 9 lists the possible data sources and modeling techniques of all FAM components. The data sources are CT scans and optical scans. The modeling techniques include the approaches to create the FAM components and the registration methods to put them together in a same coordinate system.

DETAILED DESCRIPTION OF THE INVENTION

Full Anatomy Model

FAM is defined as a collection of geometric models representing a patient's anatomical structures including jaw bones, teeth, soft tissues and nerves. FIG. 1 shows the components of a FAM. The component for soft tissues is the main differentiator. The checkmarks indicate all the applicable components for various cases. For example, the FAM of a "Fully Edentulous Lower Jaw" case will include the soft tissues, the bones and the nerves. With a fully edentulous case, there is no remaining tooth, so the components will be simply for the bones, soft tissues and nerves. For an upper jaw, there is no nerve model.

The components of a FAM are not necessarily separated geometric models. The actual embodiments can combine anatomical structures in one model or more. Specifically, it is very common that the soft tissues and teeth are combined into one model, namely, "tissue-tooth" model; the bone and teeth are combined as "bone-tooth" model. In FIG. 2, the basic embodiments of different cases are listed in a table. For example, "Partially Edentulous Upper Jaw" can have three components—a soft tissue model, a bone model and a tooth model, or two components—tissue-tooth and bone-tooth models. In the remainder of this document, the term "tissue model" will also indicate "tissue-tooth model", and "bone model" will also indicate "bone-tooth model" unless otherwise stated.

Figure 3:
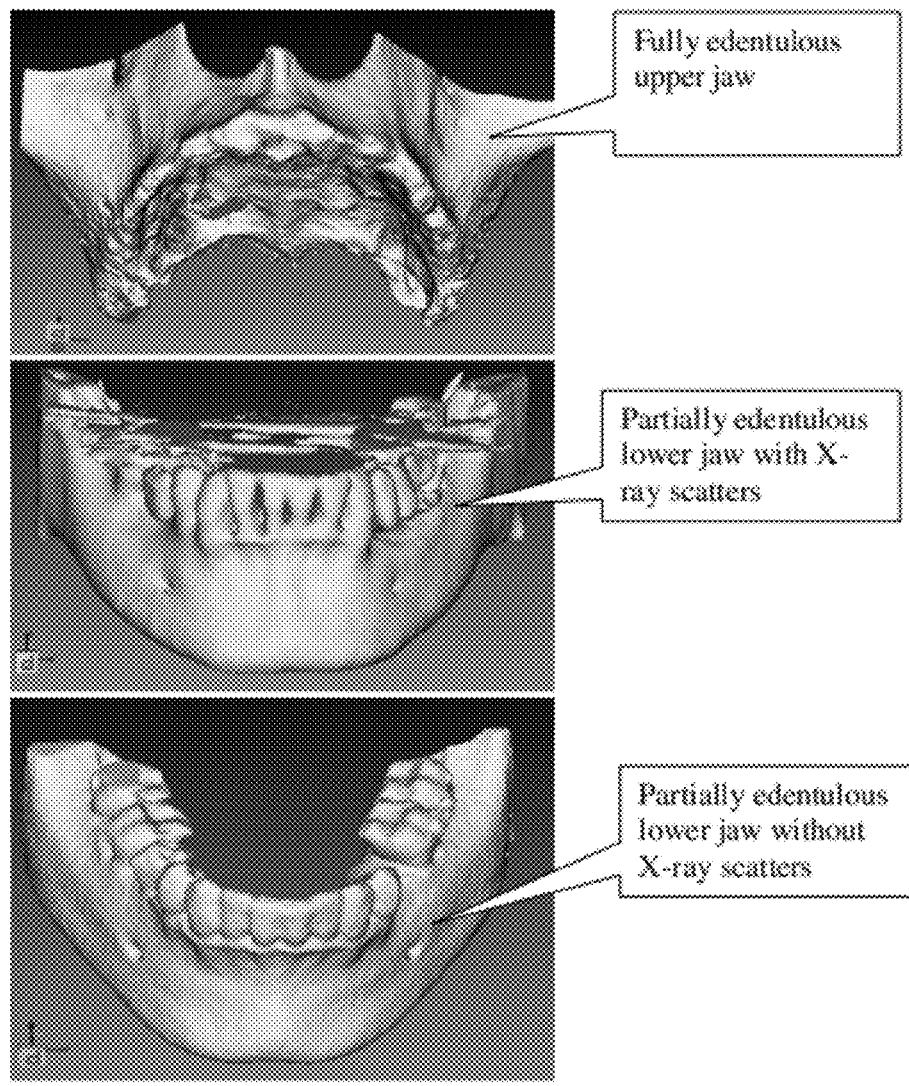
FIG. 3 shows a bone model of a fully edentulous upper jaw, a bone-tooth model of partially edentulous lower jaw with X-ray scatters, and another one without scatters.
Figure 4:
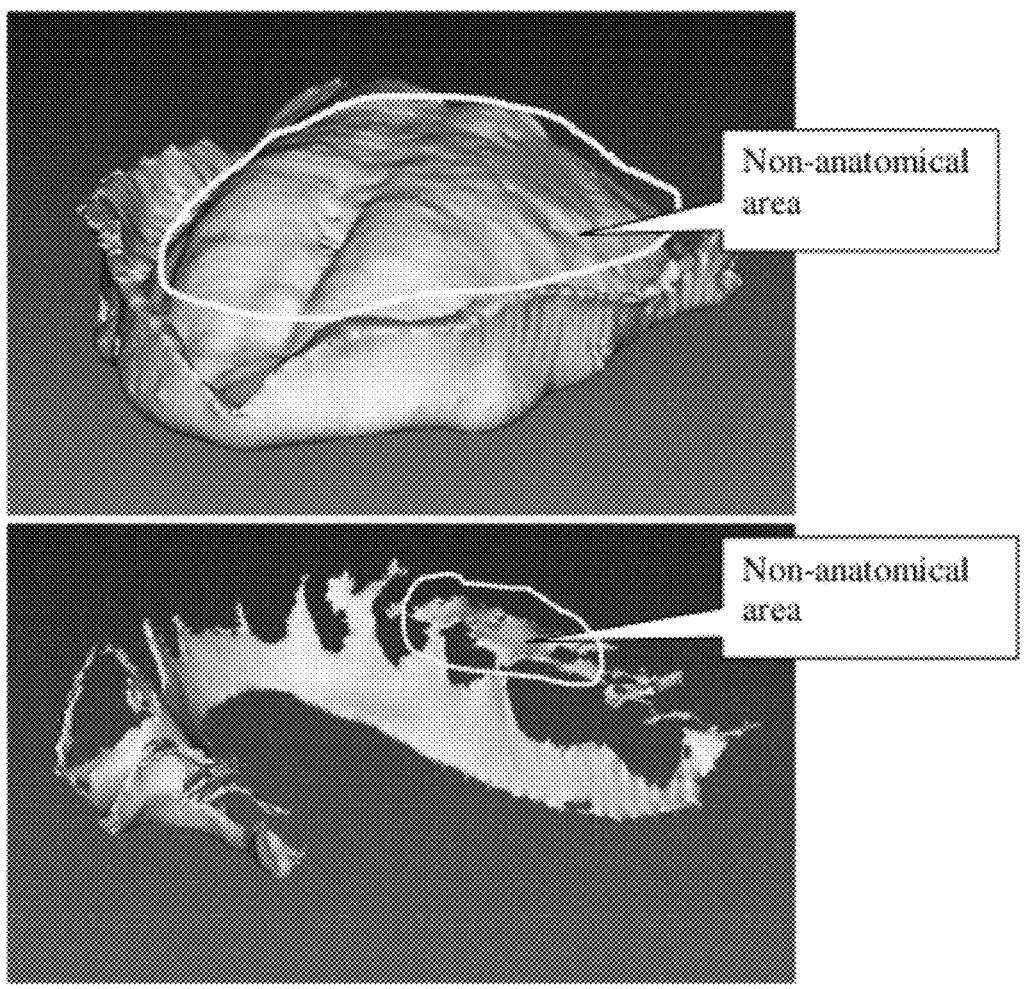
FIG. 4 shows two soft tissue models, one for a fully edentulous case, and one for partially edentulous. The models are created from scans of radiographic guides. The "non-anatomical area" may indicate both the soft tissue and the gap between the radiographic guide and the patient's oral anatomy (also shown in FIG. 5). For the second tissue model, since the radiographic guide does not extend to soft tissues at the buccal side, it has just the lingual part.
Figure 5:
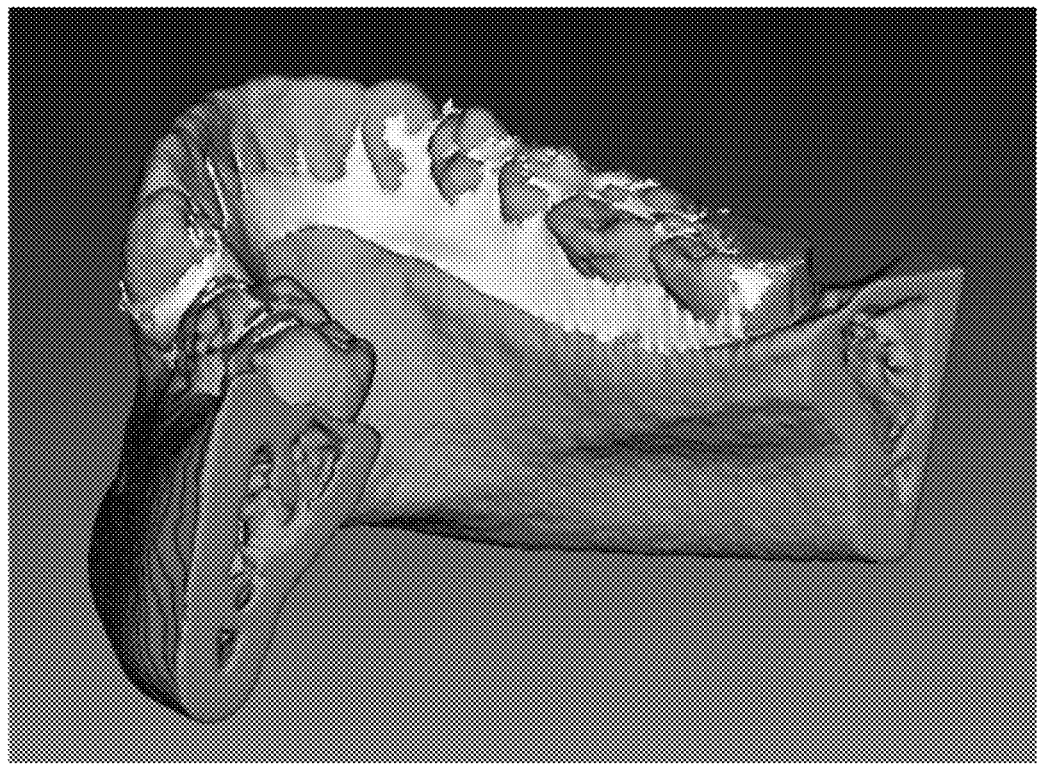
FIG. 5 shows an embodiment of a FAM assembly of soft tissue model and a bone-tooth model, which is also called a virtual stone model. The tissue model going up to the tooth surfaces actually reflects the gap between the radiographic guide and the teeth.
Figure 6:
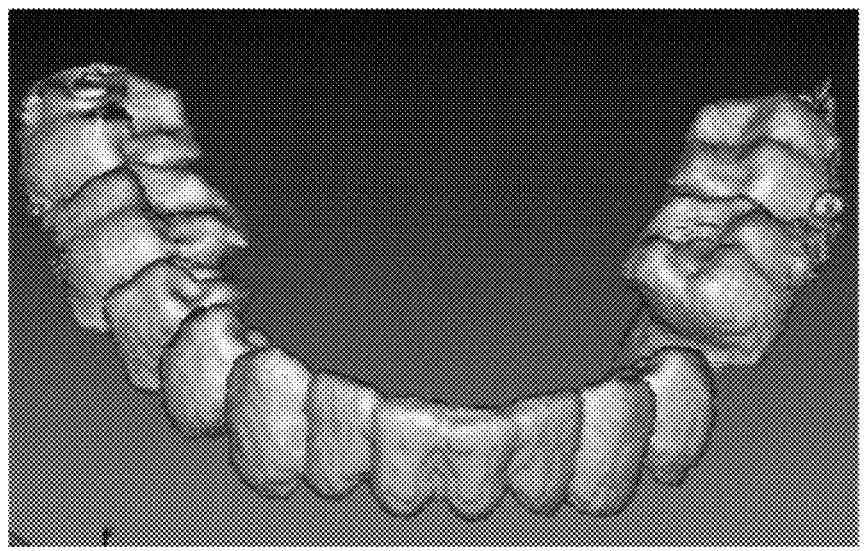
FIG. 6 shows a tooth model. The teeth in the model may only have the crown parts, or also the tooth roots.
Figure 7:
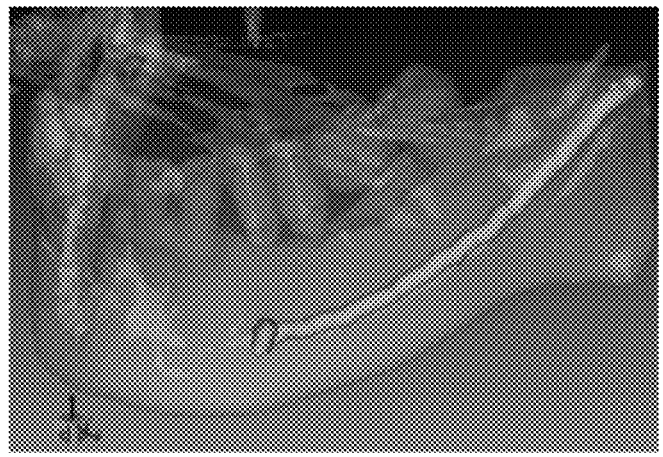
FIG. 7 shows a nerve model as a tube with a center spline.
Figure 8:
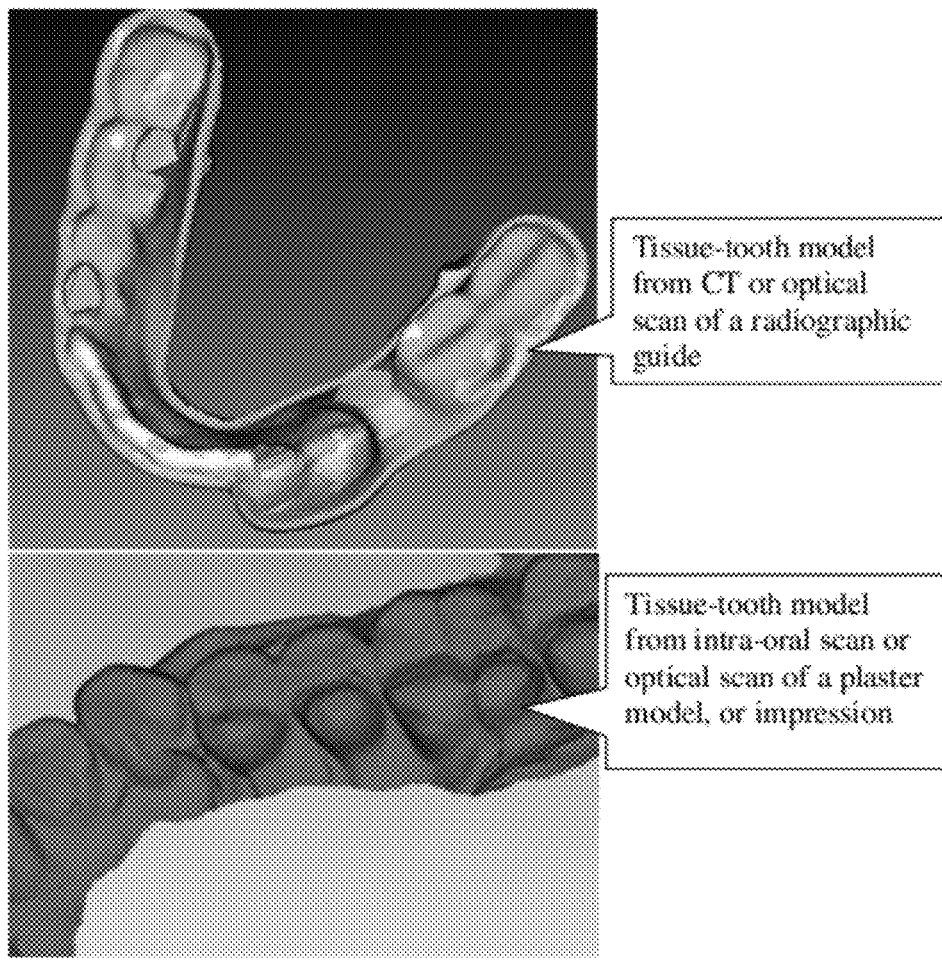
FIG. 8 shows two tissue-tooth models, one from a CT scan of a radiographic guide, one from an optical scan of a plaster model.

FIG. 3-8 gives examples of bone models, bone-tooth models, soft tissue models, tooth models, nerve models, and tissue-tooth models. Three models of bone or bone-tooth are shown in FIG. 3: a fully edentulous upper jaw, a partially edentulous lower jaw with CT scan scatters, and another one without scatters. In FIG. 4, two models are given. The first one is a soft tissue model of a fully edentulous upper jaw. The second one is that of a lower jaw. Both of them are special embodiments of tissue models. It is important that the anatomy models in this invention are used for implant treatment planning purposes other than exact duplicates of the actual anatomy, therefore the tissue models are acceptable as long as they reflect the tissues in the tooth/implant areas. The models in FIG. 4 are marked with non-anatomical areas resulted from the radiographic guides. Such areas are not exactly the soft tissue; they also reflect the space between the radiographic guide and the patient soft tissue or teeth. Since a radiographic guide may not completely fit the patient's anatomy, the gaps between them will be reflected by this tissue model. Moreover, there are some clinical cases that the radiographic guides are not well placed onto the patients jaws when the patients are being scanned. The tissue models created by this approach will also reflect such gaps. This however does not affect the implant placement and restoration preview. As a matter of fact, such a "tissue" model help identify problems like this. In the second model, the soft tissue in the buccal side is missing, because the radiographic guide—the data source—does not extend to the soft tissue area at the buccal side. FIG. 5 shows an assembly of a tissue model and a bone-tooth model. In FIG. 6 a tooth model is illustrated, which does not have the tooth roots. FIG. 7 is a nerve model shown with the jaw bone. FIG. 8 gives two tissue-tooth models. The first one is a special embodiment created from CT scan of radiographic guide, and the second one from optical scan of a stone model or an impression.

A FAM is an assembly of these components. They can be represented as a single geometric model with multiple shells, each of which can be exported as an individual file. Or, they can be a set of models. The data representation of the models can be of any format. Usually, the triangulated model is used, which represents a model as a set of triangles. The STL file format is the standard format for it.

Anatomy Modeling

The oral-dental anatomy modeling includes the approaches to acquire and create all of those components, as well as the approaches to represent the geometric data and to assemble the models together.

FIG. 9 lists all the possible data sources of the anatomy models, and the techniques to create the components. The patient CT scans are usually the data source for bones, teeth, nerves, as well as bone-tooth combinations. The term "CT scan" is used in this disclosure as a general term for all scan technologies that acquired 3D images as CT scan does, such as Cone-Beam CT (CBCT), ultra-sound, etc. The CT scans of radiographic guide (or scan template, scan prosthesis) are the data source of teeth, soft tissues, and tissue-tooth combinations as well. The optical scans of radiographic guides or plaster/impression models can be used to create tissue and tooth models. So can the patient intra-oral scans.

Usually a bone model is created by contouring the CT scan of a patient. There is a need to remove X-ray scatters as shown in FIG. 3. X-ray scatters a the areas of high density, such as tooth or metal restorations. Even though image processing techniques might be used to automate, at least partially, this process, the prevailing approach is just to let the software users manually circle some scatter areas of the bone model created by CT data thresholding, and then to remove the pixels within the areas.

Nerve models for a lower jaw are manually drawn. The users specify points on 2D CT slices, connect them with a spline, and then the software creates a tube model using it as the center.

What actually makes difference for anatomy modeling is the inclusion of tissue models and the methods to acquire and create them. The technique to create a soft tissue model from the CT or optical scan is called "virtual stone model" in this invention, which is introduced in the next section. This approach has a special step to separate soft tissues from the teeth. A simpler option will be just to create tissue-tooth models as shown in FIG. 8 in order to avoid such a step.

Because the data source of a soft tissue model is different from the CT scan of a patient, they are in different locations when put into same coordinate system. The soft tissue model needs to be registered with the bone model. The actual process can be either to register the source datasets first, or to register the models after they are created from the datasets. If a radiographic guide CT scan is used to create the soft tissue model, the guide model is registered with the bone first, and then the "virtual stone model" approach is used to create soft tissue model.

Figure 10:
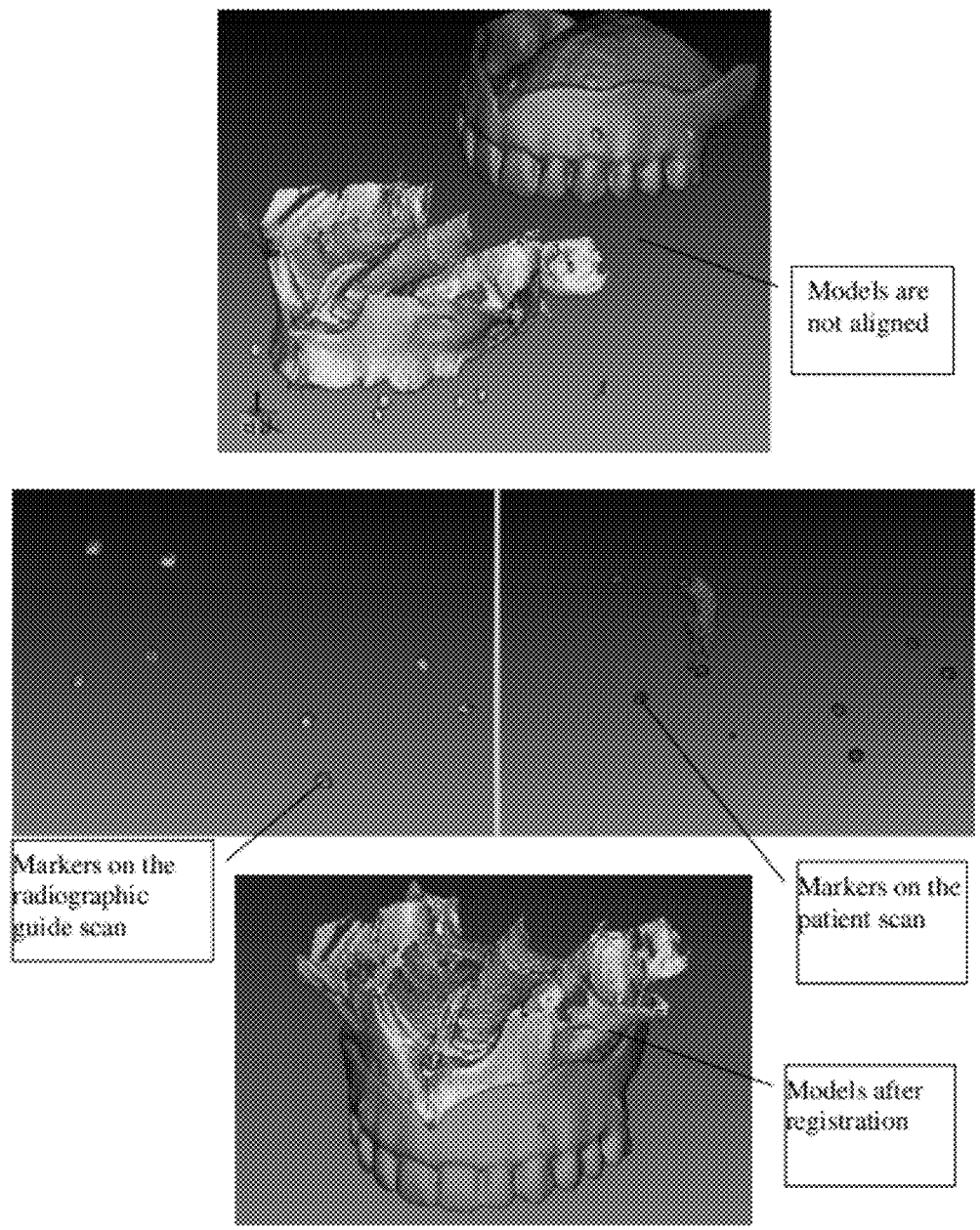
FIG. 10 illustrates the landmark-based registration process. The bone model with markers from the radiographic guide is registered with the separated scan of the radiographic guide.

The registration between the CT scan of the patient and that of the radiographic guide is based on the markers on the radiographic guide. FIG. 10 illustrates this process. The thresholding of patient scan will output both the bones and the markers since the patient is scanned wearing the radiographic guide. The bone model and the radiographic guide are not aligned at the first place. In the middle of FIG. 10, the markers with the radiographic guide scan and the patient scan are shown in different windows. The figure shows a status that the makers have not been all recognized or specified yet. Some more user interactions are needed to specify the markers in this case, because the simple thresholding technique cannot fully separate the markers from the bone structure or existing tooth restorations. Image processing can be of course employed to automatically detect the markers. Landmark based registration is applied once the markers are identified, and this finally puts the two models in the right locations as shown in the last picture of FIG. 10. Iterative Closest Point (ICP) is the most common method to register landmarks.

Figure 11:
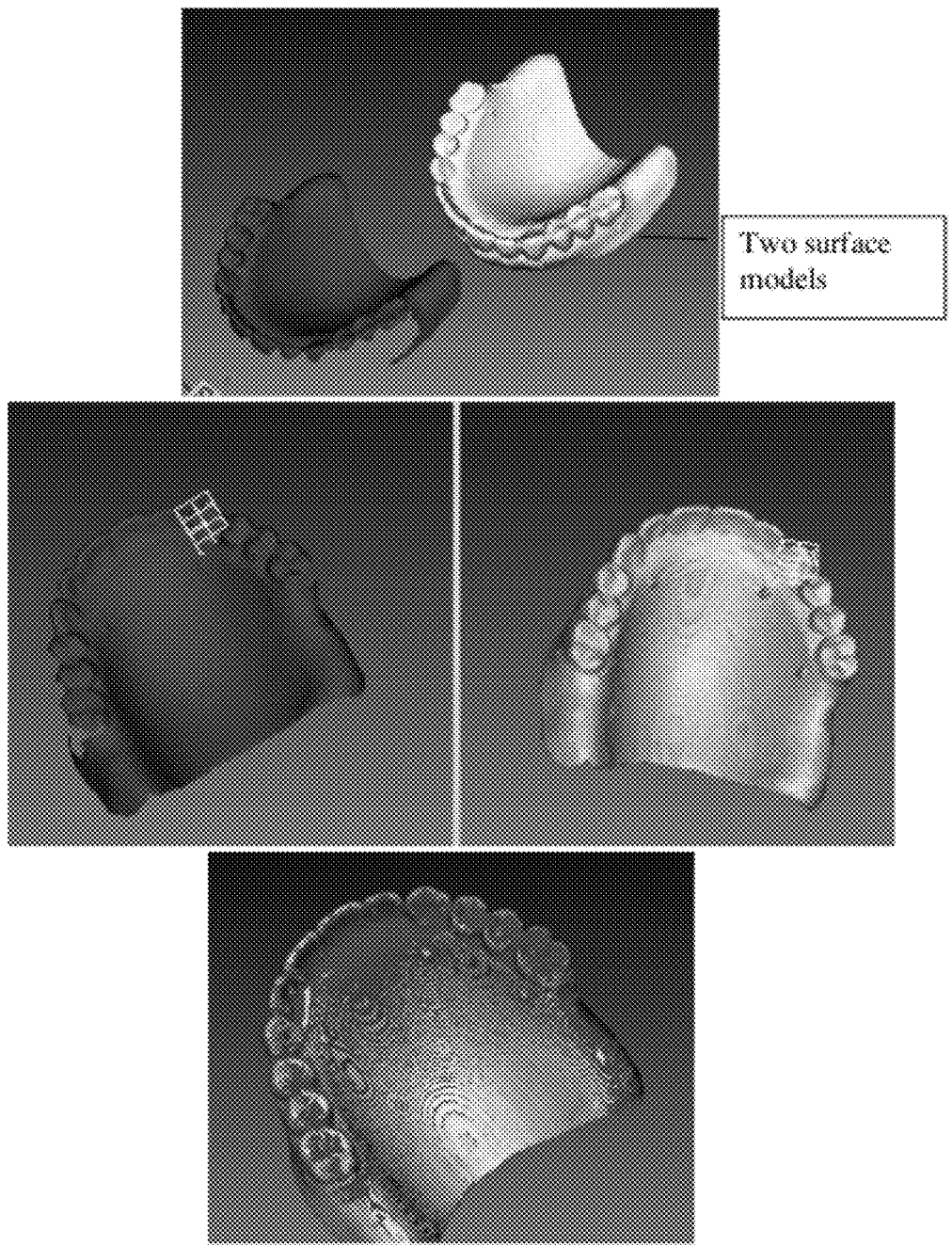
FIG. 11 illustrates the surface to surface registration.

Another scenario is the registration between two surface models, specifically, two triangulated models. FIG. 11 illustrates the surface model registration. Approaches are needed to identify the corresponding points on the two models. Improved ICP can be used for this purpose (Zhengyou Zhang, "Iterative point matching for registration of free-form curves and surfaces Source"). Some implementations can be found in public domains such as the one in Visualization Toolkit (www.vtk.org).

The possibility to perform registration determines what can be used to create the soft tissue model of a FAM. For a fully edentulous case, an optical scan cannot be used for this purpose unless a radiographic guide model also exists, because for such a case the soft tissue model from an optical scan is completely different from the bone model, and there is nothing like a marker or an overlapping area to help align them. If the radiographic guide exists, one can register the guide with the patient scan by aligning the markers, and then to register the tissue to the guide as two surface models. The reason to have such a special embodiment is that optical scan can be used to create a more accurate surgical guide. If only the radiographic guide CT scan is used, its contouring surface can have different geometry due to the different threshold values used. It is unfortunately true that a contour surface from CT scan can barely reflect the actual geometry of a model because the thresholding is very subjective (GAO Ser. No. 12/776,544). Having an optical scan in the meantime will certainly eliminate this problem.

For partially edentulous cases, the preferred embodiment is to create a bone-tooth model from the patient CT scan, and a tissue-tooth model from an optical scan, then to use the surface registration to put them together.

Virtual Stone Model

Assuming the surface model of the radiographic guide is already obtained by either CT data contouring or by an optical scan, the inward surface of the guide is treated as the surface of the soft tissues. A 3D model representing the soft tissues surrounding the bone structure is created, and combined with the bone model to form a "virtual stone model".

Figure 12:
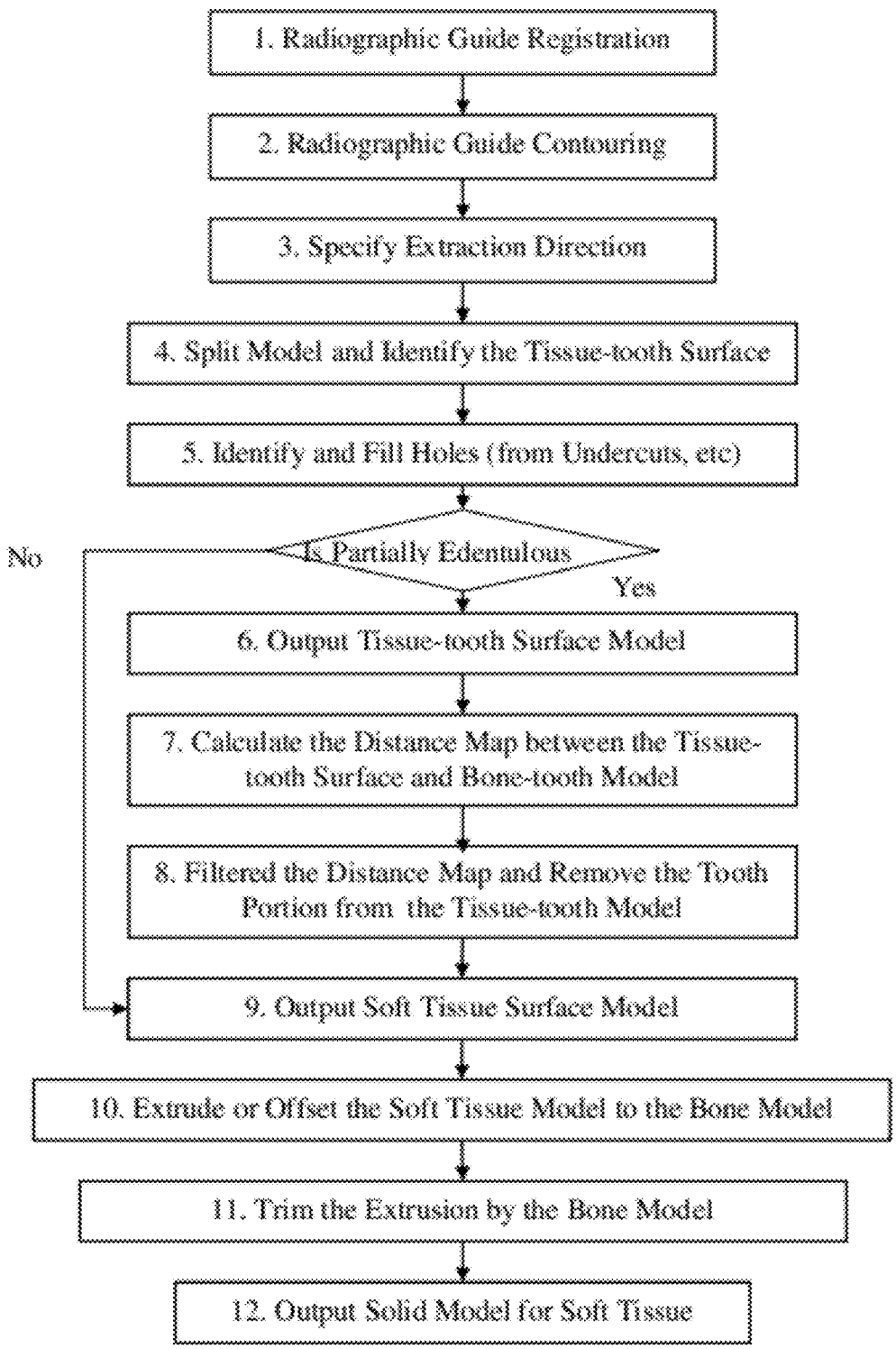
FIG. 12 shows the procedure to create a soft tissue model and a virtual stone model from the CT scan of a radiographic guide. This procedure is applicable to optical scans too with minor changes.

FIG. 12 shows how the virtual stone model is created and used in treatment planning. The steps are listed below.

Figure 13:
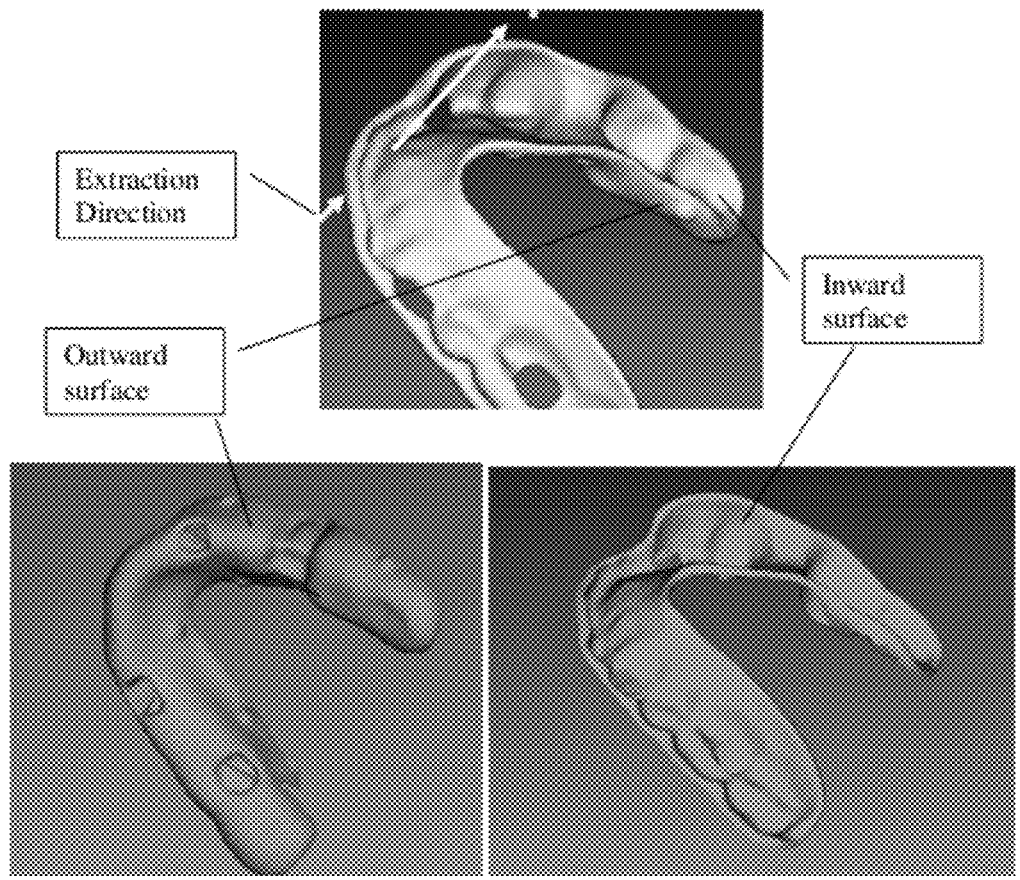
FIG. 13 defines the insert/extraction direction for the radiographic guide in order to create virtual stone model. The faces along this direction are inward directions. The model is split into two pieces with reference to this direction.
Figure 14:
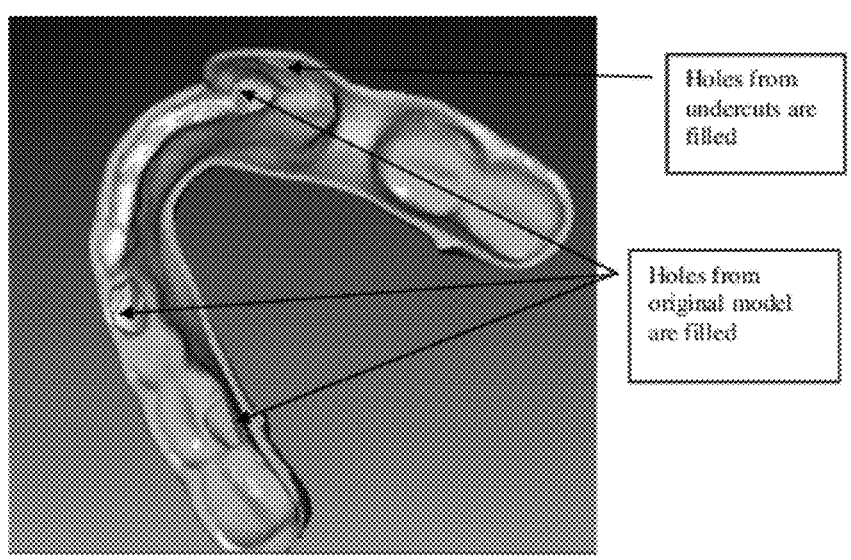
FIG. 14 illustrates the hole filling of the surface model. When the radiographic guide model is split into inward and outward surfaces, holes can occur due to undercuts. Triangles are used to fill those holes. If the original radiographic guide has holes, the results will reflect them and need to be fixed too.

1. The radiographic guide is registered with the bone structure.
2. The surface model of the guide is created by contouring the CT scan of the radiographic guide, or any other imaging technique.
3. A model view direction is defined. It is an imaginary extraction/insertion direction, along which the radiographic guide can be put into or pulled out of the patient's mouth. This is shown in FIG. 13.
4. Next, the guide model is split into two portions as shown in FIG. 13. A view direction is defined as the opposite of the direction. All faces that are "visible" along this view direction are considered part of the tissue/tooth surface. For treatment planning purposes, this surface will serve as the tissue model, even though this model is more or less a "wrapper" of the tissue and tooth surfaces.
5. Along the defined view direction, some triangles of the inner surface may not be fully visible. They are called undercuts, which will leave holes on the model when the inner surface is extracted. The algorithm to fill the holes is a common technique in polygonal modeling. An example can be found in "A piecewise hole filling algorithm in reverse engineering" by Y Jun. The result is illustrated in FIG. 14.
6. For fully edentulous cases, go to step 9. For partially edentulous, output the resulted surface model as tissue-tooth model.
7. A distance map between this model and the bone-tooth model is then evaluated. In a triangulated surface model, a vertex is represented as its coordinate and a scalar value. In order to represent the distance map, the scalar value is set to the distance between an extracted model vertex and the bone-tooth model.
8. The tooth areas are identified through filtering the distance map. If a vertex is on the tooth area, its distance value should be close to zero within a tolerance. All the vertices and their triangles together can then be removed from the model.
9. Output the resulted model as the surface model of the soft tissues.
10. This tissue model is then offset or extruded toward the bone structure.
11. The result is then trimmed by the bone model.
12. Output this as 3D virtual soft tissue model.

As shown in FIG. 4, the resulted solid model is actually the volume between the radiographic guide and the bone structure. When the guide is made with good accuracy and fits well with the patient anatomy, this model can well represent the patient's soft tissues. Together this tissue model and the patient bone structure including the remaining teeth make the so-called "virtual stone model", a variation of FAM as shown in FIG. 5.

When the tissue-tooth model is from optical scan, the same procedure is applied to create the virtual stone model. The procedure is actually simpler. After the registration, the distance map is evaluated, and the rest is same as step 7 and after.

The virtual stone model differentiates itself from the conventional plaster model or its optical scan because the anatomical components are separately represented, and they can be also manufactured with rapid prototyping or 3D printing.

Treatment Planning System

In an implant treatment planning system based on the anatomy modeling, the FAM is in the center of the workflow. The system has the following major logical components. The anatomy modeling module takes CT and optical scans as inputs, and creates a FAM with various modeling tools. The FAM management and visualization modules manage all the models and their display. The implant placement module places implants with references to the FAM. The restoration preview module performs aesthetics evaluations by previewing the implants and adding virtual teeth and the like. The surgical guide design module creates guides based on FAM.

FAM serves as three roles. The first is called placement reference. The software system lets the users to place implants onto this model. In the prior art the implants are not placed with references to such a model reflecting the actual patient anatomy with soft tissues and remaining teeth. Instead, the 2D slices of CT scan or 3D bone models are used for this purpose.

Figure 15:
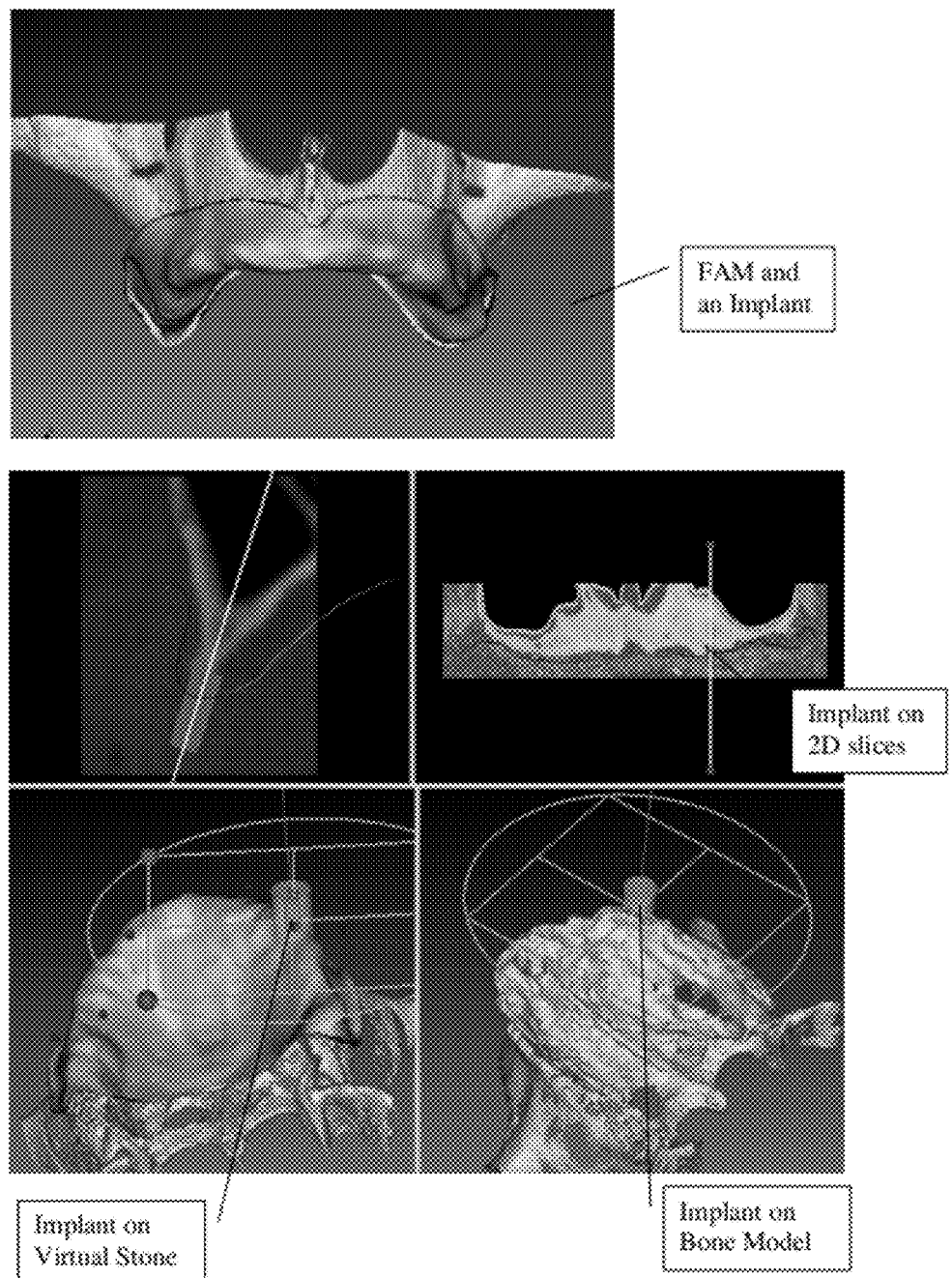
FIG. 15 shows a FAM, an implant, and how the implant placement is performed with the 2D slices, the 3D FAM window, and the 3D bone model.

FIG. 15 illustrates how an implant is placed with a FAM as reference. In 3D graphics window the components of the FAM are displayed. Each of them can be set visible or invisible. In the meantime, there are 2D views, which display the CT scan of the patient, and the cross sections of the FAM components. When a panoramic view is desired, the 2D views will also display the reformatted cross sections defined by the specified arch curve. The implant placement is performed on all the 2D and 3D views. The implants are displayed as 3D models in 3D windows and cross sections in 2D. Each view of an implant will have a placement widget attached. There are both 2D and 3D versions of the placement widgets. The users can use any placement widget in one view to adjust an implant's position, and all the other views will be updated accordingly.

There are also tools to change the display properties of individual components, such as opacity, color, lighting, etc. A model navigator accompanying the graphics views uses a tree structure to show the FAM components and other objects created, and to provide individual controls to the models (GAO, US patent application Ser. No. 12/795,045).

Figure 16:
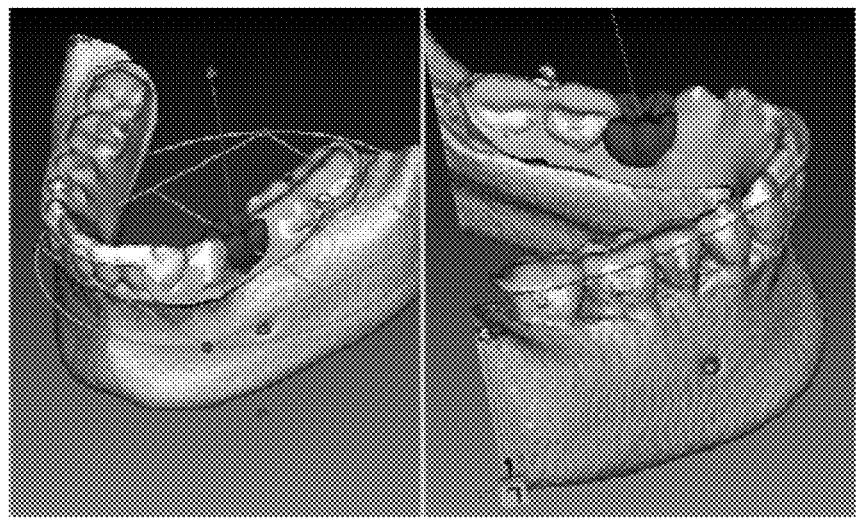
FIG. 16 illustrates the restoration preview based on FAM. A virtual tooth is placed onto a FAM. Used as the aesthetics reference, a FAM is more informative for the users to evaluate the treatment plan.

Secondly, FAM serves as an aaesthetics reference, the reference to preview implants and restorations. Abutments, virtual teeth, etc. are added to FAM so that the users can better preview a case with the soft tissues simulated. FIG. 16 shows a case that a virtual tooth is being added to the FAM. Its size and location are being adjusted. The essential difference between this process and existing approach is that the users get instant feedback or preview on how the implants and virtual teeth look like since the soft tissues are shown in the scene. This function to perform restoration preview with soft tissues is one of the goals of this invention. Without FAM, the software systems cannot provide an appropriate 3D preview tool to assess the aaesthetics of a treatment plan. Using a radiographic guide model for preview, as in some implementations, is much more problematic, because it is made by offsetting the patients' anatomy.

Thirdly, FAM is the base for designing and making surgical guides, and thus called the surgical guide reference. With prior art, there are two methods to create surgical guides. When a radiographic guide model is available, a surgical guide is created from this model by adding implant holes and additional form features to it. When there is no radiographic guide, i.e., a bone level surgical guide is to be designed, and bone model or bone-tooth model is used as the base for surgical guide design. The areas surrounding the implants are clipped, offset and then modified with form features.

Figure 17:
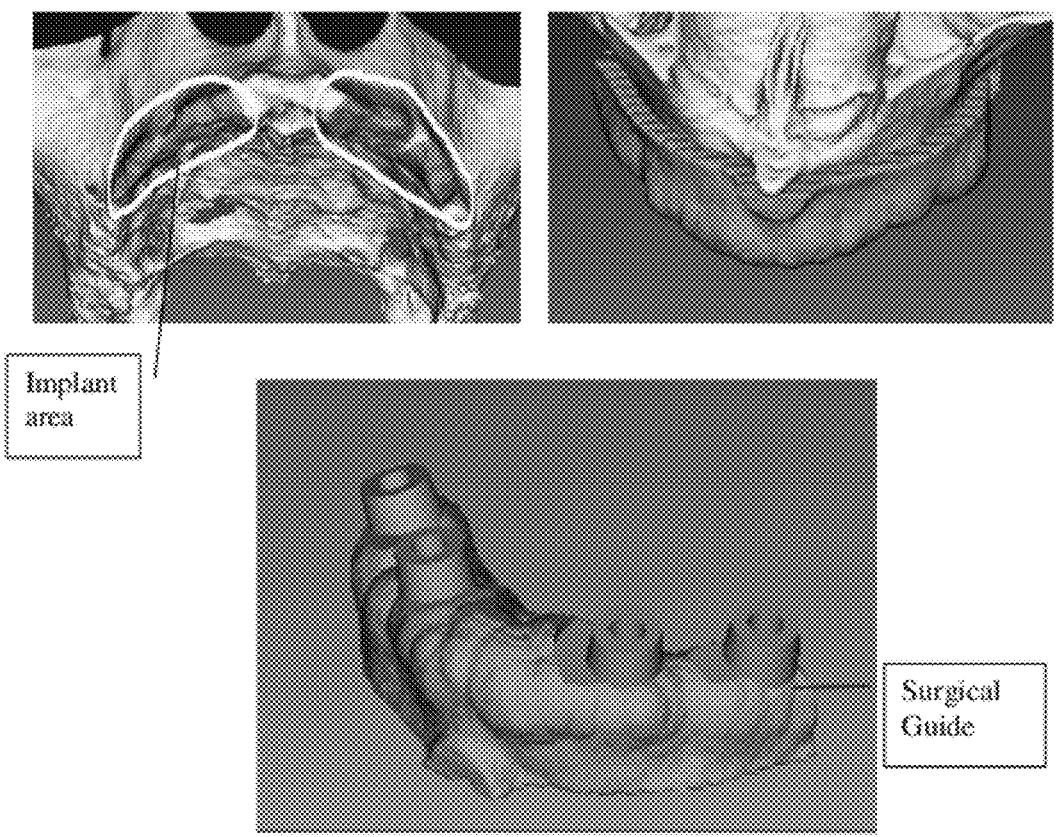
FIG. 17 illustrates the major steps to create a surgical guide from FAM. A bone-level guide case. The implant areas on a FAM are identified first, then extracted, offset and modified. The resulted surgical guide model can be further designed with CAD software.
Figure 18:
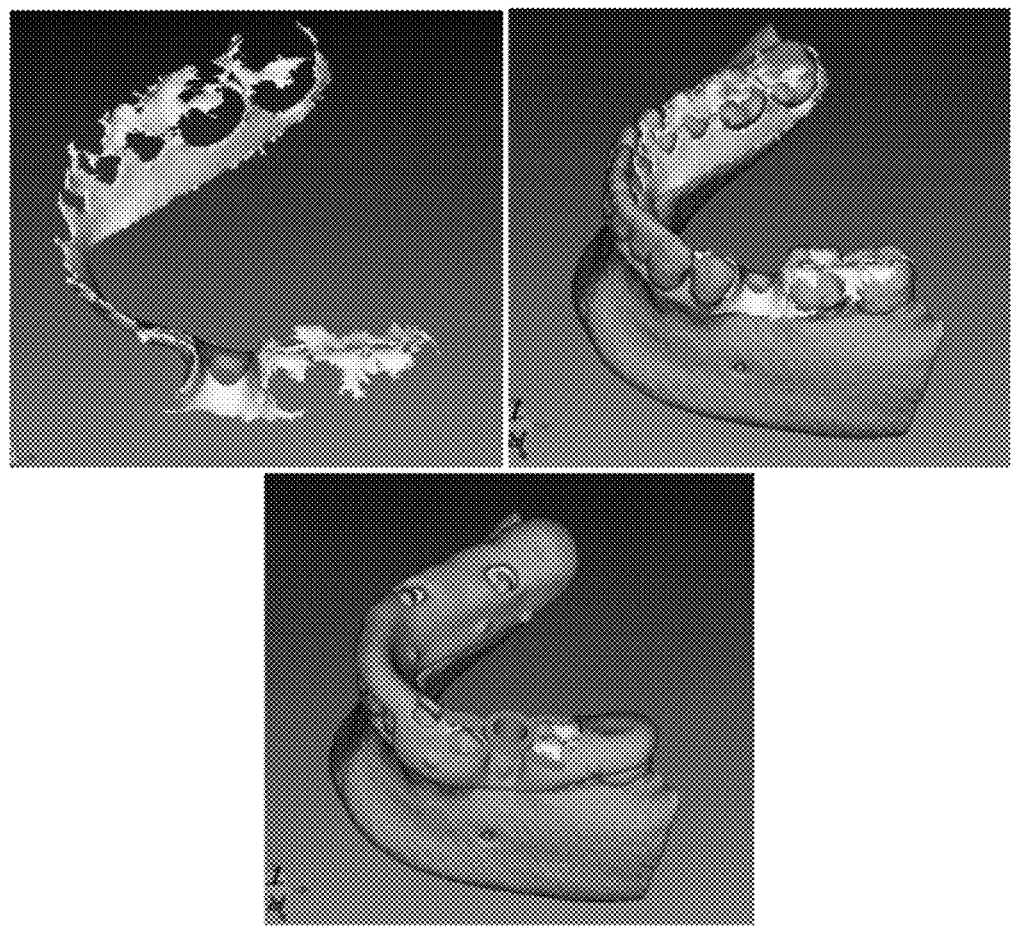
FIG. 18 shows the design of a surgical guide with FAM. The implant hole is created on the FAM, and the surgical guide is generated from the radiographic guide model or FAM. The guide model is then placed onto the FAM for further evaluation.

FAM, especially with soft tissue models from optical scans or bone level (without tissue model) cases, can lead to different surgical guide design and manufacturing methods in addition to the afore-mentioned options. In one specific embodiment, the virtual stone model is used as a base to design a surgical guide. The components of the virtual stone model are united together as a single solid model first, then the area surrounding the implants is clipped and extracted. This area is then offset by a given thickness. Form features like implant holes, irrigation windows, fillets, etc. are added to the model. Further model modifications can be also done using a CAD system until the surgical guide model is as desired. This is a generic approach that works for all scenarios. FIG. 17 illustrates a simple bone-borne surgical guide case. The implant areas are marked in the first picture, the extracted area is offset as shown in the second picture and a surgical guide is created afterwards. In FIG. 18, the tissue model and virtual stone model are also modified with implant holes. The surgical guide is automatically generated and shown in the third picture.

Alternatively, it is possible to create a "master model" using FAM, with which conventional manufacturing method can be used to make a surgical guide. A simple embodiment of master model includes a virtual stone model with implant holes on it, and implant inserts that can be placed into these implant holes. The FAM also enables the combination of digital treatment planning and physical model based planning. This is disclosed in "A Hybrid Method for Dental Implant Treatment Planning" (Gao, US application Ser. No. 12/860,019).

Figure 19:
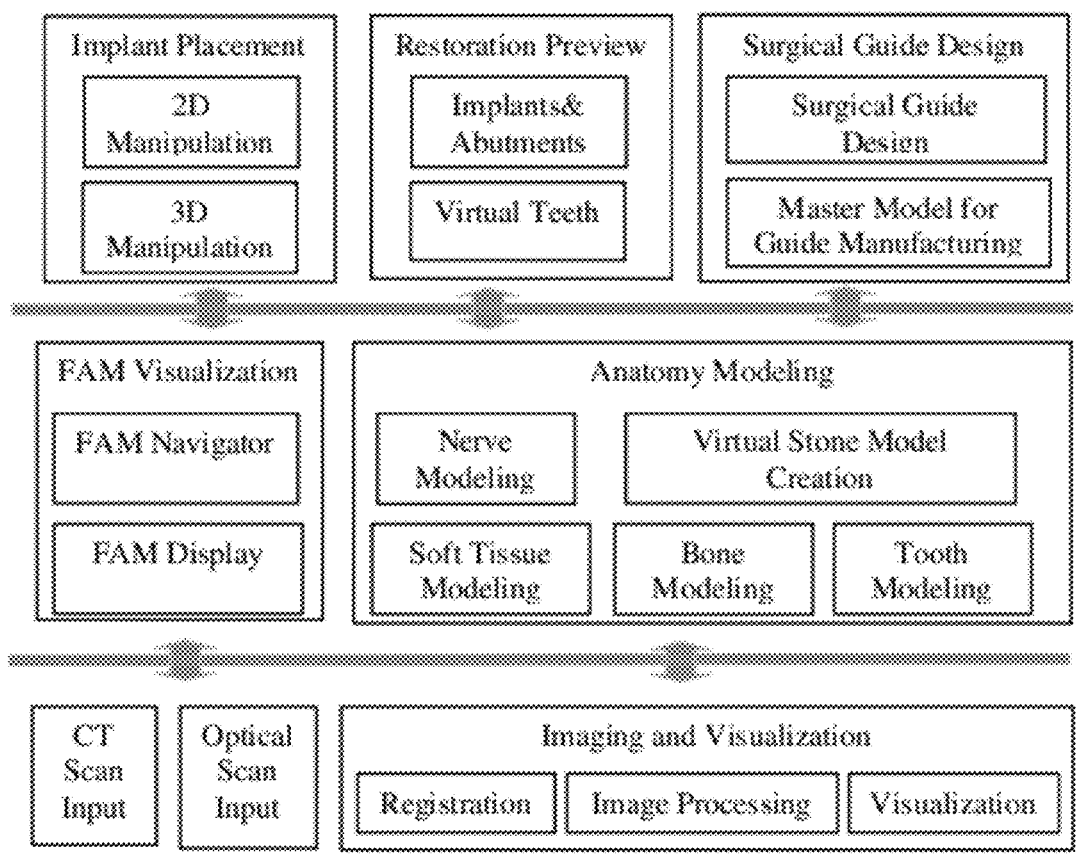
FIG. 19 illustrates the logical hierarchy of a treatment planning system based on anatomy modeling. As prior art, the system is built upon the basic file I/O, image processing and visualization modules. What makes difference is that the FAM creation and navigator, which serves as the base for treatment planning, restoration preview and surgical guide design. All of those activities use the FAM as a unique reference throughout the workflow.

The logical components and the hierarchy of the treatment planning system based on FAM are shown in FIG. 19. Starting from the bottom of the figure is the system core level including the components of image data file I/O, image processing, visualization and registration. The center layer is FAM creation and management. An optional FAM navigator gives users an easy way to access and manage FAM components. It can also control the display of the FAM. In the anatomy modeling modules, FAM components and virtual stone models are created. In the treatment planning layer are Implant Placement, Restoration Preview, and Surgical Guide Design.

A treatment planning system is considered based on anatomy modeling or FAM if one of the following is true:
A soft tissue model or virtual stone model is created before the treatment planning starts.
The implant placement uses a soft tissue model as reference in addition to bone and nerve models.
The restoration preview is also based on FAM, essentially, on a tissue model. The models of implants, abutments and crowns are all placed onto a FAM so that the preview is performed with a tissue model presenting.
The system creates either surgical guide models or master models from FAM.

What is claimed is:
1. A computer system for dental implant treatment planning and surgical guide design based on a full anatomy model, comprising:
  A. a computer hardware system with an operating system,
  B. an interactive computer software that is saved to a non-transitory computer readable medium, which, generates images and graphics shown on a display of the computer, and performs the treatment planning simulation and surgical guide design, wherein:
    i. the full anatomy model comprising, bone, teeth, and nerve model as well as a virtual stone model is created from CT scans and/or optical scans of a patient,
    ii. implant treatment planning is performed with said full anatomy model,
    iii. the surgical guide is designed based on said anatomy model.
  C. a geometric modeling system provided to create virtual stone model from CT scan of a radiographic guide, comprising both anatomy surface data and information for surgical guide design, wherein the virtual stone model is created by:

i. registering the radiographic guide with the bone structure,
ii. creating the surface model of the guide by contouring the CT scan of the radio graphic guide, or other imaging technique,
iii. defining a model view direction as an extraction/insertion direction along which the radiographic guide can be put into or pulled out of the patient's mouth,
iv. splitting the guide model into two portions,
v. completing the polygonal modeling technique to fill holes on the model from undercuts,
vi. for fully edentulous case go to step vii and for partially edentulous case:
  1) output the result as a tissue-tooth model,
  2) a distance map between the tissue-tooth model and the bone tooth model is evaluated to create a triangulated surface model, a vertex is represented as its coordinate and a scalar value and in order to represent the distance map and the scalar value is set to the distance between an extracted model vertex and the bone-tooth model,
  3) identify tooth areas through filtering distance map wherein if a vertex is on the tooth area its value should be close to zero and all the vertices and their triangle can then be removed from the model,
vii. the resulted output is the surface model of the soft tissue,
viii. the model is offset or extruded towards the bone structure,
ix. the result is trimmed by the bone-tooth model;
D. whereby the system tools for implant planning, virtual restoration preview and surgical guide design are all based on the virtual stone model as a common reference.

2. The computer system of claim 1, wherein
A. the geometric modeling system creates the base geometry of the virtual stone based on one or more input data sources to represent the soft tissue and, if applicable, tooth surfaces of a patient,
B. a means is provided to associate the virtual stone model with a direction, which defines the insert direction of a surgical guide,
C. the geometric modeling system further processes the virtual stone model with said direction where all faces that are visible along this view direction are considered part of the tissue/tooth surfaces,
D. the virtual stone model is further evaluated and assigned a distance map between this model and the bone-tooth model in addition to the geometry data,
E. a visualization system is provided to visualize the distance map, and
F. said distance map is visualized along with the virtual stone model, whereby treatment planning and surgical guide design are performed with said virtual stone model.

3. The computer system of claim 2, wherein
A. a user interaction tool is provided to define a direction, along which the radiographic guide can be put into or pulled out of the patient's mouth,
B. the geometric modeling system creates the virtual stone model from the CT scan of a radiographic guide by extracting the adaption surface of the radiographic guide that touches a patient's soft tissue and, if applicable, tooth surfaces, and
C. a treatment planning system places implants and virtual teeth onto the virtual stone model so as to have a more realistic preview than onto the radiographic guide.

4. The computer system of claim 3, further including
A. a surgical guide design system creating surgical guide digital model using the virtual stone model as a base model, with the steps comprising
  I. offsetting the base model and creating a solid model, and
  II. adding drill holes and additional form features to said solid model, whereby the surgical guide is designed based on the virtual stone model other than the radiographic guide.

5. The computer system of claim 3, wherein a system is provided to visualize the distance map between the virtual stone model and the patients, which can reflect the gaps between radiographic guide and the patient's jaw when the radiographic guide is not well placed.

6. A computer system for dental implant treatment planning and surgical guide design based on a full anatomy model, comprising:
A. a computer hardware system with an operating system,
B. an interactive computer software that is saved to a non-transitory computer readable medium, which, generates images and graphics shown on a display of the computer, and performs the treatment planning simulation and surgical guide design, wherein:
  iv. the full anatomy model comprising, bone, teeth, and nerve model as well as a virtual stone model is created from CT scans and/or optical scans of a patient,
  v. implant treatment planning is performed with said full anatomy model,
  vi. the surgical guide is designed based on said anatomy model,
C. a geometric modeling system provided to create virtual stone model from optical scan of soft tissue and tooth surfaces, comprising both anatomy surface data and information for surgical guide design, wherein the virtual stone model is created by:
  i. registering the optical scan with the bone-tooth structure,
  ii. defining a model view direction as an extraction/insertion direction along which the surgical guide to be designed can be put into or pulled out of the patient's mouth,
  iii. completing the polygonal modeling technique to fill holes on the model from undercuts,
  iv. finishing the tissue model as following:
    1) outputting the result as a tissue-tooth model,
    2) a distance map between the tissue-tooth model and the bone-tooth model is evaluated to create a triangulated surface model, a vertex is represented as its coordinate and a scalar value and in order to represent the distance map, and the scalar value is set to the distance between an extracted model vertex and the bone-tooth model,
    3) identify tooth areas through filtering distance map wherein if a vertex is on the tooth area its value should be close to zero and all the vertices and their triangle can then be removed from the model,
  v. the tissue model is offset or extruded towards the bone structure,
  vi. the result is trimmed by the bone model giving the virtual 3D soft tissue model,
D. whereby the system tools for implant planning, virtual restoration preview and surgical guide design are all based on the virtual stone model as a common reference.

7. The computer system of claim 6, wherein
A. the geometric modeling system creates the base geometry of the virtual stone model based on one or more input data sources to represent the soft tissue and, if applicable, tooth surfaces of a patient,
B. a means is provided to associate the virtual stone model with a direction, which defines the insert direction of a surgical guide,
C. the geometric modeling system further processes the virtual stone model with said direction—where all faces that are visible along this view direction are considered part of the tissue/tooth surfaces,
D. the virtual stone model is further evaluated and assigned a distance map between this model and the bone-tooth model in addition to the geometry data,
E. a visualization system is provided to visualize the distance map, and
F. said distance map is visualized along with the virtual stone model, whereby treatment planning and surgical guide design are performed with said virtual stone model.

8. The computer system of claim 7, wherein
A. the geometric modeling system creates virtual stone model from a surface scan of a patient's tissue or plaster model when there are sufficient remaining tooth surface in the patient's mouth that can be used as landmarks to align the surface scan with the CT scan of the patient,
B. a user interaction tool is provided to define a direction, along which the surgical guide can be put into or pulled out of the patient's mouth, and
C. a treatment planning system places implants and virtual teeth onto the virtual stone model.

9. The computer system of claim 8, further including
A. a surgical guide design system creating surgical guide digital model using the virtual stone model as a base model, with the steps comprising
   i. offsetting the base model and creating a solid model, and
   ii. adding drill holes and additional form features to said solid model, whereby the surgical guide is designed based on the virtual stone model other than the surface scan of soft tissue and teeth.

* * * * *